(12) United States Patent
Paatero et al.

(10) Patent No.: US 8,974,673 B2
(45) Date of Patent: Mar. 10, 2015

(54) METHOD OF REGENERATION AN ORGANIC EXTRACTION SOLUTION THAT HAS BEEN USED IN A LIQUID-LIQUID EXTRACTION PROCESS

(75) Inventors: Erkki Paatero, Helsinki (FI); Kai Jyrkkä, Kokkola (FI); Sami Virolainen, Lappeenranta (FI)

(73) Assignee: Outotec Oyj, Espoo (FI)

( * ) Notice: Subject to any disclaimer, the term of this patent is extended or adjusted under 35 U.S.C. 154(b) by 452 days.

(21) Appl. No.: 13/376,907

(22) PCT Filed: May 26, 2010

(86) PCT No.: PCT/FI2010/050425
§ 371 (c)(1),
(2), (4) Date: Dec. 8, 2011

(87) PCT Pub. No.: WO2010/142841
PCT Pub. Date: Dec. 16, 2010

(65) Prior Publication Data
US 2012/0080382 A1 Apr. 5, 2012

(30) Foreign Application Priority Data
Jun. 11, 2009 (FI) .................................... 20090238

(51) Int. Cl.
*B01D 15/00* (2006.01)
*C22B 3/30* (2006.01)
(Continued)

(52) U.S. Cl.
CPC ................ *C22B 3/02* (2013.01); *C07C 249/14* (2013.01); *B01F 7/00441* (2013.01); *B01F 7/24* (2013.01); *B01F 13/1013* (2013.01);
(Continued)

(58) Field of Classification Search
CPC .... C07C 249/08; C07C 249/14; C22B 3/0017
USPC ......... 210/634, 638, 660, 669, 681, 683, 690; 564/264; 423/24
See application file for complete search history.

(56) References Cited
U.S. PATENT DOCUMENTS 3,764,622 A * 10/1973 Kuntschik et al. ............ 564/264
4,104,359 A    8/1978 Davis et al.
(Continued)

FOREIGN PATENT DOCUMENTS
CN         1110329 A        10/1995

OTHER PUBLICATIONS
International Search Report (PCT/ISA/210) issued on Oct. 1, 2010, by Finnish Patent Office as the International Searching Authority for International Application No. PCT/FI2010/050425.
(Continued)

*Primary Examiner* — Matthew O Savage
(74) *Attorney, Agent, or Firm* — Buchanan, Ingersoll & Rooney PC

(57) ABSTRACT

The invention relates to a method and apparatus for restoring the extractive potential of organic hydroxyoxime-based extraction solution used in the recovery of metals by liquid-liquid extraction. The method is two-stage, in which an aqueous solution of hydroxylamine or some hydroxylamine compound is used in the reaction stage, and the removal of the undesirable compounds generated in the reaction occurs in the second stage by adsorption purification. The reaction stage and the adsorptive stage are carried out in a mixing tank.

21 Claims, 5 Drawing Sheets

Figure 1:
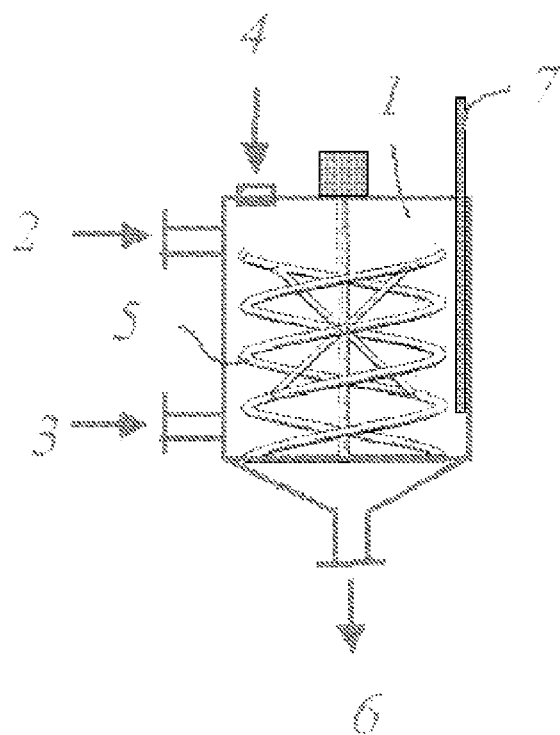

(51) Int. Cl.

| | |
|---|---|
| *C22B 3/02* | (2006.01) |
| *C07C 249/14* | (2006.01) |
| *B01F 7/00* | (2006.01) |
| *B01F 7/24* | (2006.01) |
| *B01F 13/10* | (2006.01) |
| *C07C 249/08* | (2006.01) |
| *C22B 3/26* | (2006.01) |
| *C22B 15/00* | (2006.01) |

(52) U.S. Cl.
CPC .......... *B01F 13/1016* (2013.01); *C07C 249/08* (2013.01); *C22B 3/0005* (2013.01); *C22B 3/0017* (2013.01); *C22B 3/0032* (2013.01); *C22B 15/0084* (2013.01); *C22B 15/0089* (2013.01)

USPC ............ 210/669; 210/683; 210/690; 564/264

(56) References Cited

U.S. PATENT DOCUMENTS

| | | | |
|---|---|---|---|
| 4,873,369 A * | 10/1989 | Fuchs | .......................... 564/264 |
| 5,185,081 A | 2/1993 | Nyman et al. | |
| 5,488,161 A | 1/1996 | Krbechek | |
| 5,993,757 A | 11/1999 | Virnig et al. | |

OTHER PUBLICATIONS

E. Jaaskelainen et al., Adsorption of hydroxyoxime-based extractants on silica and mica particles in copper extraction processes, Hydrometallurgy 49, 1998, pp. 151-166.

\* cited by examiner

METHOD OF REGENERATION AN ORGANIC EXTRACTION SOLUTION THAT HAS BEEN USED IN A LIQUID-LIQUID EXTRACTION PROCESS

FIELD OF THE INVENTION

The invention relates to a method and apparatus for restoring the extractive potential of an organic hydroxyoxime-based extraction solution used in the recovery of metals by liquid-liquid extraction. The method is two-stage, in which an aqueous solution of hydroxylamine or some hydroxylamine compound is used in the reaction stage, and the removal of the undesirable compounds generated in the reaction occurs in the second stage by adsorption purification. The reaction stage and the adsorptive stage are carried out in a mixing tank.

BACKGROUND OF THE INVENTION

Liquid-liquid extraction is used generally in metal separation processes, allowing metals to be extracted from aqueous solution using organic extraction solutions. An extraction solution consists of an extraction reagent and a hydrocarbon solvent. The extraction reagent is generally diluted in the kind of hydrocarbon solvent that dissolves into an aqueous solution or evaporates into air as little as possible in process conditions.

The composition of both the active extraction reagent and its hydrocarbon solvent in the extraction solution has been found to change during long-term industrial use. As a result, the metal-binding power of some extraction reagents may have worsened. In particular this has been observed in copper extraction processes and nickel extraction processes using various reagents based on hydroxyoxime derivatives. The reagents mentioned are also used for the extraction of certain other metals and metalloids (e.g. palladium and germanium) as well as in some synergistic extraction reagent mixtures to modify the selectivity for different metals. Changes have also been found to occur in the composition of the hydrocarbon solvent. It is known that hydrocarbon solvents oxidise slowly and generate among other things surface-active long-chain carboxylic acids.

It has been known previously that a hydroxyoxime reagent used in extraction, which has degraded in the hydrolysis reaction into aldehyde or ketone, may be reoximated using hydroxylamine ($NH_2OH$) or a salt thereof. The reoximation reaction takes place as follows:

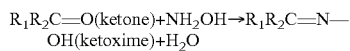

If $R_2$=H in the formula, the source material in question is some aldehyde and the product the corresponding aldoxime. If $R_2$ is for example an alkyl or aryl group, it concerns a ketone and ketoxime. This same equilibrium reaction from right to left, in other words acid-catalysed hydrolysis, is one of the decomposition reactions that occurs when hydroxyoxime is used as the extraction reagent in the extraction process. However, it is known that hydroxyoximes also decompose e.g. in oxidation reactions.

It is disclosed in U.S. Pat. No. 4,104,359 that organic sulphonic acid causes the degradation of an α-hydroxyoxime reagent in the organic phase. According to the patent, α-hydroxyoxime can be reoximated in the above-mentioned mixture directly using a solid hydroxylamine salt. According to the patent, the method can also be used for β-hydroxyoximes, which are ketoximes (current copper extraction reagents often belong to the aldoximes). The patent also mentions that alternatively a saturated aqueous solution of hydroxylamine may be used for the purpose and the process may be performed for instance in a mixer-settler-type of extraction cell. However, there are no practical examples in the patent of the implementation in which a saturated aqueous solution is used directly. As shown later in the examples of this patent application, the method accordant with the U.S. patent would be very slow and the conversion in it would remain low. In addition, undesirable reactions also take place in reoximation and consequently, the settling of the phases for instance is very slow. The implementation method accordant with this reference publication without a purification step is therefore not satisfactory technically.

A method is disclosed in U.S. pat. No. 5,993,757 that also covers β-hydroxyoximes, which may be either ketoximes or aldoximes. According to the method, the hydroxyoxime extractant that has decomposed into ketone or aldehyde is reoximated using an aqueous solution of a hydroxylamine salt. The patent differs from the earlier patent so that one of the patent claims is for a distillation purification stage before reoximation and the use of a phase transfer catalyst in the reoximation reaction. The reaction time is 5 - 36 hours. As stated later in the examples of this patent application, both distillation and the use of a phase transfer catalyst can be avoided. Likewise the reaction can be implemented considerably faster and operated in a continuous flow mode.

PURPOSE OF THE INVENTION

The purpose of this invention is to present a method and apparatus which enable to avoid the problems with the methods described in the prior art. Now it has been observed for instance that the regeneration of the extraction solution should be performed in two stages, i.e. the harmful surface-active substances generated during treatment in the extraction solution treated with hydroxylamine in the reaction stage should be removed after treatment, and this occurs most advantageously in a second stage by means of adsorption purification. Thanks to adsorption purification, the phases of the liquid-liquid extraction process, the aqueous and organic phases, settle or separate from each other far faster than solutions that have not been subjected to adsorption purification.

SUMMARY OF THE INVENTION

The essential features of the invention will be made apparent in the appended claims.

The invention relates to a method for treating an organic extraction solution used in liquid-liquid extraction, where the extractant of the solution is hydroxyoxime-based and the metal extraction properties of which have changed chemically in the process conditions. In order to restore the physical and metal extraction properties of the extraction solution essentially to the original level, the treatment of the extraction solution takes place in two stages. The first stage is a reaction stage, in which the extraction solution is contacted with an aqueous solution of hydroxylamine or a compound thereof, so that the aldehydes and/or ketones formed in the extraction solution in process conditions are reoximated and after which the solutions are separated. The extraction solution is treated in a second or adsorption purification stage, in which the extraction solution is contacted with an adsorption material in solid form, enabling the purification of the extraction solution from the compounds of harmful substances generated in the reaction stage.

The adsorption material in solid form is preferably at least one of the following: bentonite, diatomite, aluminium silicate, metal oxide, activated carbon, polymeric adsorbent and polymeric ion exchange resin.

The hydroxylamine compound used for reoximation is at least one of the following: hydroxylamine sulphate, hydroxylamine halide, hydroxylamine phosphate or hydroxylamine sulphonic acid. According to one preferred embodiment of the invention, the amount of hydroxylamine or the amount of hydroxylamine in the compound thereof used in the reaction stage is at least equivalent to the total amount of aldehyde and/or ketone formed in the extraction solution.

The pH of the hydroxylamine-containing solution routed to the reaction stage is regulated to the region of 1-10. Preferably the pH of the hydroxylamine-containing solution routed to the reaction stage is regulated to the region of 4-9. At least one of the following is used for pH control: an alkali metal hydroxide, an earth alkali metal hydroxide, an alkali metal carbonate, an earth alkali metal carbonate, ammonia, or an aqueous solution thereof and mineral acid.

The extraction solution is comprised of an extraction reagent and a hydrocarbon solvent, whereby the active, metal-binding component of the extractant is hydroxyoxime derivative, the oxime group of which is either an aldoxime or ketoxime in structure. According to one embodiment of the invention, the extraction solution is comprised of an extraction reagent and a hydrocarbon solvent, in addition to which the extraction solution includes an organic modifying agent that belongs to at least one of the following groups: alcohol, phenol, ester, diester, ether, diether, ketone, amide or nitrile.

According to one embodiment of the invention, a hydroxylamine-containing aqueous solution is recycled to utilise the hydroxylamine or compound thereof effectively. In accordance with the invention the hydroxylamine may be recovered from the aqueous solution by means of a cation exchange resin. According to the invention the concentration of aqueous hydroxylamine is monitored by acid-base titration.

According to one embodiment of the invention, the amount of adsorption material is 0.01-10 weight %. According to one preferred embodiment of the invention, the amount of adsorption material is 0.5-3 weight %. The adsorption material is separated from the extraction solution by settling, filtering or centrifuging. According to one preferred embodiment of the invention, the adsorption material is fed into the adsorption stage in ground form. Adsorption material may also be fed into the adsorption stage in powder, spherical or fibre form.

According to one embodiment of the invention, the reaction stage and adsorption stage occur as batch operations. According to another embodiment of the invention, the reaction stage and adsorption stage take place as continuous operations. According to a third embodiment of the invention, the reaction stage takes place as a batch operation, but the adsorption stage is continuous. According to yet another embodiment of the invention, the reaction stage is run continuously but the adsorption stage is a batch operation.

The invention also relates to an apparatus for treating organic extraction solution used in liquid-liquid extraction, where the extraction reagent of the solution is hydroxyoxime-based and the metal extraction properties thereof have changed chemically in process conditions. In order to restore the physical and metal extraction properties of the extraction solution, the extraction solution is treated in two stages. In the first stage, the reaction stage, the mixing of the extraction solution to be reoximated and an aqueous solution of hydroxylamine or a compound thereof occurs in a mixing tank, which is equipped with a spiral-shaped mixer. After the reaction stage, the solutions are separated from each other and the extraction solution is treated in the second stage, i.e. the adsorption purification stage, in which the mixing of the extraction solution and the adsorption material in solid form is performed with a spiral-shaped mixer.

A pH electrode is preferably installed in the apparatus accordant with the invention, enabling the measurement of the pH of the aqueous hydroxylamine solution. According to one preferred embodiment, the pH electrode is located in the mixing tank of the reaction stage.

According to one embodiment of the invention, the apparatus consists of one mixing tank, so that both the reaction stage and the adsorption stage are carried out in the same mixing tank. According to another embodiment of the invention, the apparatus is made up of two mixing tanks: the reaction stage mixing tank and the adsorption stage mixing tank. According to a third embodiment of the invention, the apparatus comprises at least one mixing tank and at least one settling tank connected to it. According to yet another embodiment of the invention, the settling tank of the reaction stage is equipped with members for recycling the aqueous solution to the reaction stage mixing tank.

According to one embodiment of the invention, the settling tank of the apparatus functions as the extraction solution storage tank.

LIST OF DRAWINGS

Figure 2:
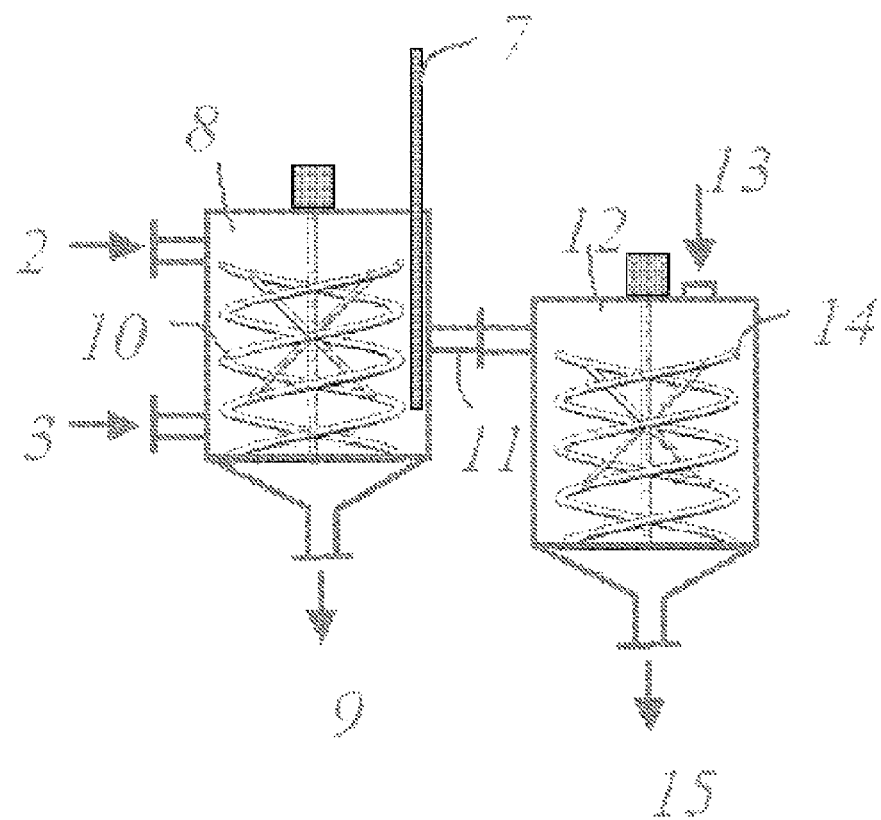
Figure 3:
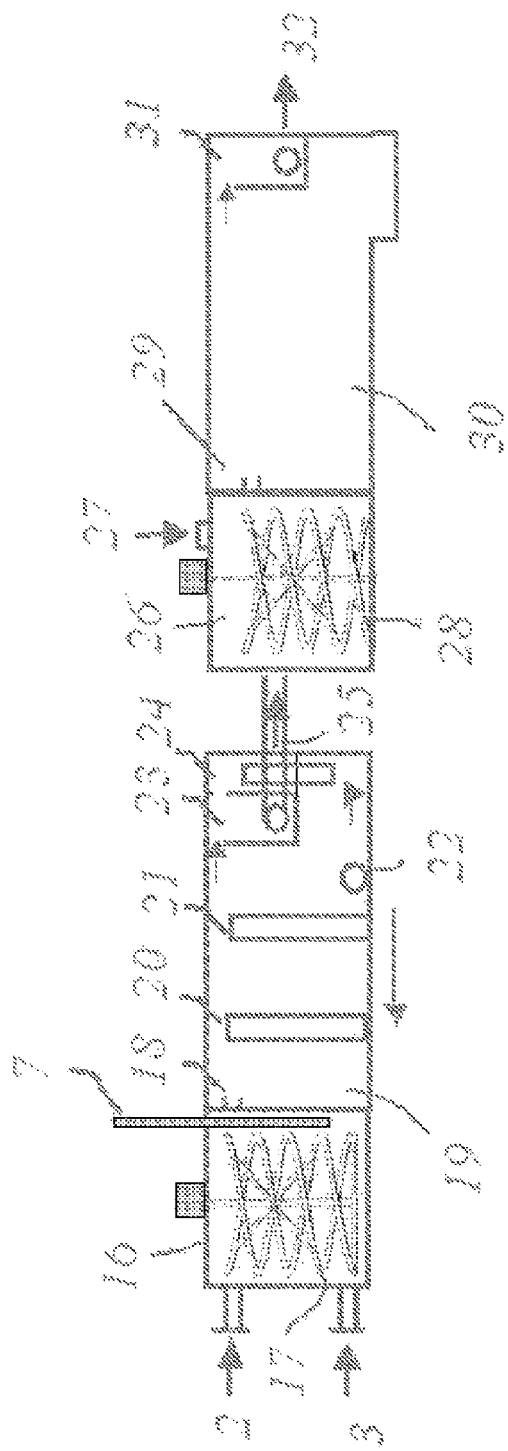
Figure 4:
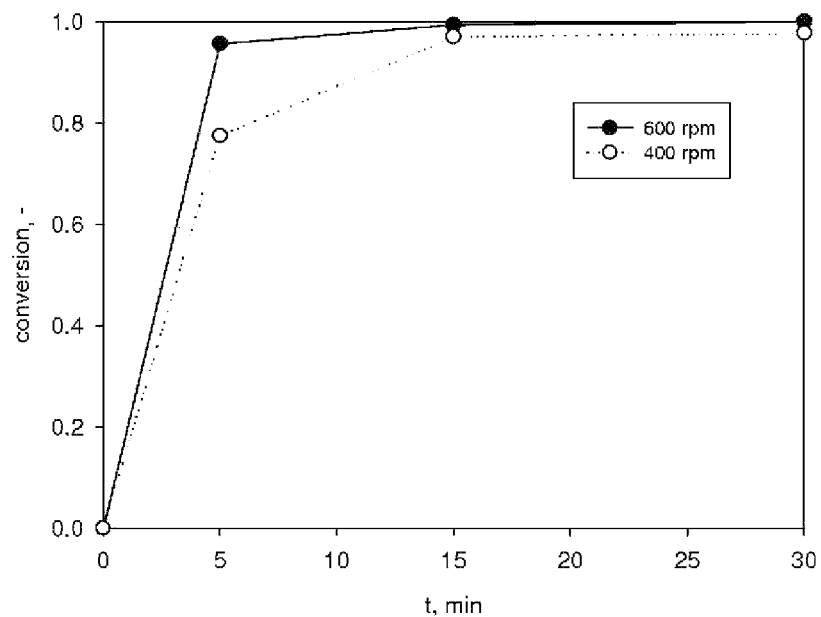
Figure 5:
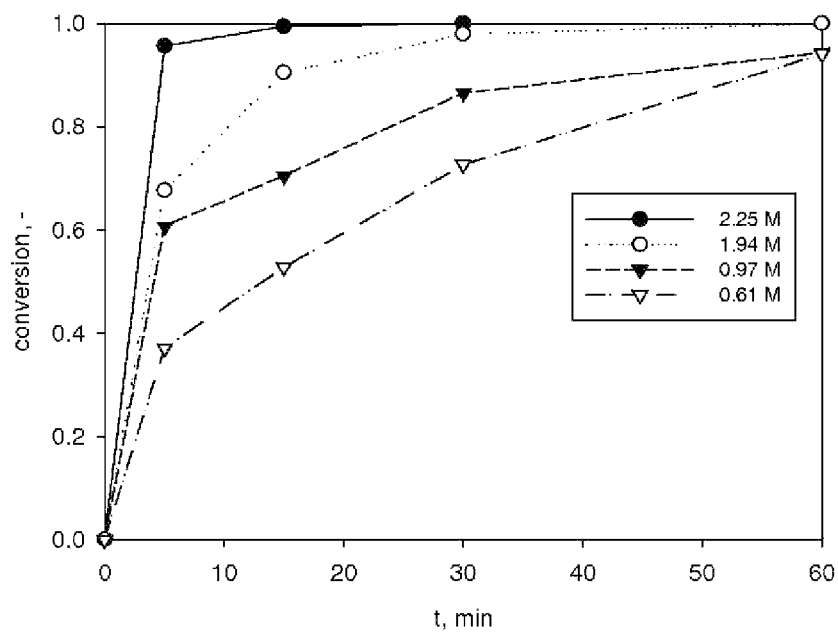
Figure 6:
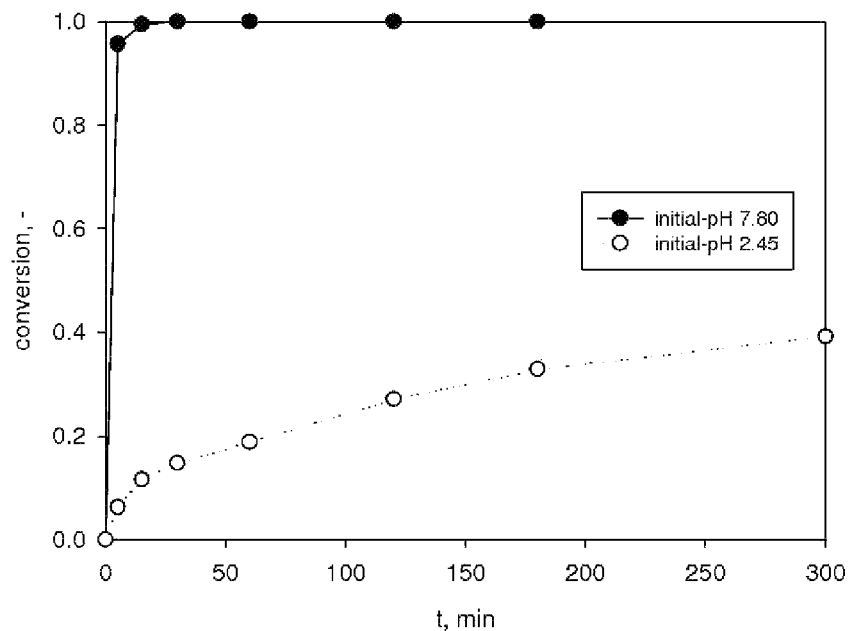
Figure 7:
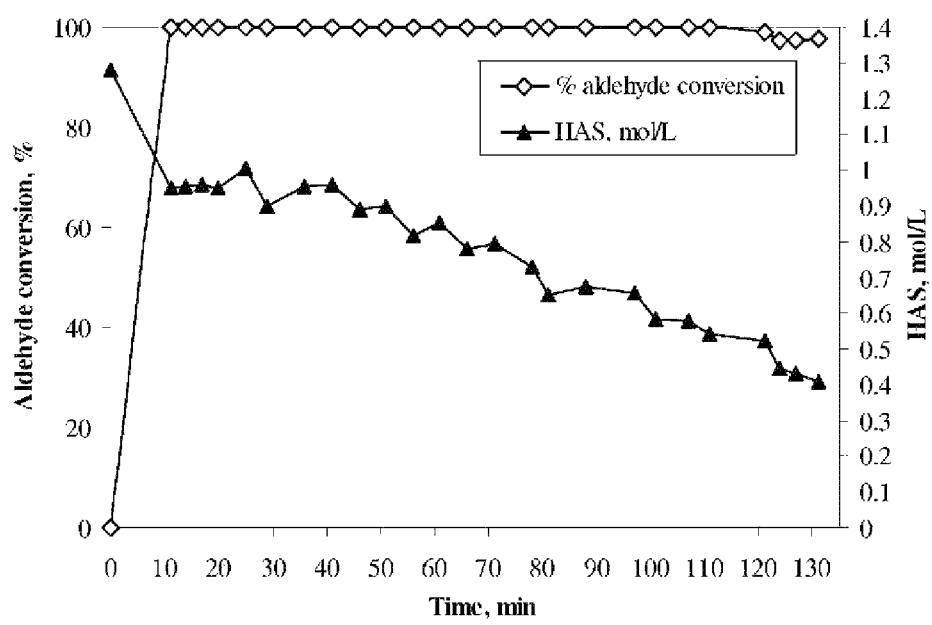

FIG. 1 is a principle drawing of one equipment configuration accordant with the invention, FIG. 2 is a principle drawing of another equipment configuration accordant with the invention, FIG. 3 is a principle drawing of a third equipment configuration accordant with the invention, FIG. 4 is a graphical presentation of the effect of the rotational speed of the mixer on the conversion of the extraction solution reoximation reaction as a function of time, FIG. 5 is a graphical presentation of the effect of the reoximation reagent concentration on the conversion of the extraction solution reoximation reaction as a function of time, FIG. 6 presents the effect of the pH value on the conversion of the extraction solution reoximation reaction as a function of time, and FIG. 7 presents the results of the reoximation reaction carried out in continuous flow mode as a function of time.

DETAILED DESCRIPTION OF THE INVENTION

The method and apparatus accordant with the invention enable the restoration of the extractive properties of the active part of the extraction solution used in metal extraction, i.e. the organic extraction reagent, to correspond partially or completely to the properties of a new unused reagent. In the solution now developed the treatment of the extraction phase or extraction solution takes place in two stages, i.e. in the reaction stage the extraction solution is treated with a reoximation reagent and adsorption purification is performed in the second stage. Extraction solution mostly consists of an extraction reagent and a hydrocarbon solvent, but in addition there may be an organic modifying agent present in the extraction solution, belonging to the following group: alcohol, phenol, ester, diester, ether, diether, ketone, amide or nitrile.

The reoximation reagent used is hydroxylamine. For practicality and safety it is often advantageous to use some hydroxylamine compound such as for instance hydroxylamine hydrochloride, hydroxylamine sulphate or hydroxylamine sulphonic acid. In the many known industrial syntheses, the most commonly used salt is hydroxylamine sulphate i.e. hydroxyl ammonium sulphate $(H_2NOH)_2H_2SO_4$. It is generally available commercially either in solid form or often as a 25 weight % aqueous solution. In the method accordant with the invention, no phase transfer catalyst is used to accelerate the reaction nor is there distillation before hydroxylamine treatment as disclosed in U.S. Pat. No. 5,993,757, but instead the removal of impurities takes place after the reaction stage by adsorption purification.

In the metal recovery process, used and partially degraded extraction solution can be routed according to the method to the mixing tank as a side stream, where it is treated in continuous flow operation, or the reagent can be treated periodically in batches in an apparatus accordant with the invention. The extraction solution is routed into contact with the reoximation reagent, which is in the form of an aqueous solution. There is preferably a surplus of aqueous solution of hydroxylamine or of the salt thereof in respect of the quantity of extraction solution and in particular the degradation products (aldehyde or ketone) of its extraction reagent in the aqueous solution. This is a case of a two-phase reaction, so the reaction requires continuous effective mixing of the dispersion formed of the solutions. Both in laboratory tests and above all in plant-scale tests it was observed that in order to achieve a good reoximation result, mixing should be effective enough that the reaction time is reduced. Since this is a liquid-liquid reaction, after the reaction the settling of the phases ought to be rapid. The spiral-shaped mixing member disclosed in U.S. Pat. No. 5,185,081 was found to be very suitable for this purpose. The diameter of the mixing member therein is almost as large as the inner diameter of the reaction vessel. Mixing is effective over the whole zone, but it avoids high shear rates and the formation of an emulsion. After an adequate reaction time, the aqueous phase, which contains the hydroxylamine surplus to the reaction, is separated from the organic phase. The same aqueous solution can be recycled in treatment several times simultaneously adding hydroxylamine to replace that consumed in the reaction.

The reaction time of the reoximation stage depends in particular on the pH of the aqueous solution and the concentration of the hydroxylamine reagent. A higher pH speeds up the reaction, but incurs neutralisation costs. Likewise, if a saturated (approx. 30 weight %) aqueous solution of hydroxylamine sulphate is used, the speed of the reaction is high, but for operational safety and in order to avoid undesired precipitation dilution may be appropriate, and the concentration is preferably between 10-25 weight %. The reaction time may thus be under 6 minutes at the shortest, but typically between 10-90 min and the temperature between 20-90° C., preferably between 40-60° C.

The pH of the aqueous solution is regulated either before the reaction or during it to a value that in the reaction stage is between 1 and 10. Preferably, however, the pH value is between 4 and 9. So that the pH of the aqueous solution remains in the desired range, it is advantageous to equip the reaction stage mixing tank with pH electrodes and instruments for feeding in the regulating reagent. For neutralising the solution, for instance alkali- or earth alkali hydroxide, alkali- or earth alkali metal carbonate or ammonia may be used. Particularly if a free hydroxylamine base is used in the reaction stage, the pH of the solution may be higher than desired and in that case some mineral acid, typically sulphuric acid, is used for regulating the pH value.

The volumetric ratio of the organic phase and the aqueous phase is not crucially important and may vary in a wide range between 1:50 and 50:1. In practice it is generally preferred that the phase ratio in the mixing reactor is between 1:4 and 4:1.

In the adsorption purification subsequent to the reaction stage, the extraction solution is purified of the side-products generated in the hydroxylamine reaction by means of a solid, preferably fine-ground adsorbent material. Preferably the material is some clay mineral based adsorbent, e.g. acid-activated bentonite i.e. montmorillonite clay or diatomite. The purpose of the adsorbent is to remove the undesired compounds from the solution phase onto the surface of the adsorption material. Afterwards the adsorbent is separated from the solution for instance by settling, filtration or centrifugation and the treated extraction solution can be returned to the metal recovery process. The use of bentonite and diatomite is known at copper extraction plants in what is termed crud treatment, but in conjunction with this invention adsorption purification was unexpectedly observed to have the beneficial effect of removing the harmful compounds generated in the hydroxylamine reaction. It was found in the tests carried out that according to the invention the surface-active harmful substances of the hydrocarbon solvent of the extraction solution were also removed as a result of hydroxylamine treatment and adsorption purification, in other words the reoximation and purification accordant with the invention target both the extraction reagent and the hydrocarbon solvent components of the extraction solution.

Adsorption purification may be implemented either in the same reactor as the reaction stage or in another separate reactor vessel after it. The mixing in the adsorption stage should also be effective, because for instance bentonite forms a viscous suspension to some extent with the extraction phase. The proportion of adsorbent in the suspension is between 0.01 and 10 weight %, preferably at least between 0.5 and 3 weight %. The adsorbent is separated from the solution for example by settling, filtration or centrifugation.

FIGS. 1-3 show three alternative embodiments of the apparatus accordant with the invention for combining the reaction stage and the adsorption stage. In FIG. 1 both the reaction stage and the adsorption stage take place in the same mixing tank 1. The extraction solution to be treated is fed into the reactor through feed conduit 2 and the hydroxylamine-containing aqueous solution through feed conduit 3. The reaction occurs as a two-phase reaction, and to optimise it the reaction mixture is preferably mixed with a spiral-shaped mixing member 5. The pH value of the aqueous phase is measured from the dispersion using pH electrode 7. The electrode according to the drawing is located in the mixing tank, but as in practice pH measurement of a dispersion of organic phase and aqueous phase may be awkward, pH measurement can also be carried out either on the settled aqueous solution or on the hydroxylamine solution before the reactor for instance in a stirred circulation tank for the aqueous hydroxylamine solution when the reoximation takes place in continuous flow mode. Furthermore, the concentration of hydroxylamine can be monitored and controlled based on analysis of the aqueous phase. After the reaction stage the liquid phases are allowed to settle. The concentration of HAS is analysed from the aqueous phase and HAS is added to compensate the amount consumed in the reaction. HAS is monitored by acid-base titration.

The settled aqueous phase is discharged through discharge conduit 6 and the organic phase remains in the reaction vessel. The fine-grained adsorbent material for the adsorption purification stage is charged into the reactor via conduit 4 and adsorption is optimised by mixing the suspension. Finally, the suspension of extraction solution and adsorbent is discharged from the reaction vessel via discharge conduit 6 for settling, filtration or centrifugation. The hydroxylamine solution used in the reaction stage can be used again partially or completely, because only some of the hydroxylamine is consumed in the reaction between the extraction solution and the aqueous solution. The hydroxylamine in the aqueous solution that is removed from the circuit is recovered advantageously by means of a cation exchange resin.

FIG. 2 depicts another alternative embodiment of the invention, in which the reaction stage takes place as in FIG. 1 as a batch reaction in mixing tank 8, which is equipped with spiral-shaped mixing member 10 and pH electrode 7. After the reaction stage, the settled aqueous hydroxylamine solution is removed completely or partially from mixing reactor 8 via discharge conduit 9. The settled organic phase is routed via connection pipe 11 to adsorption purification stage mixing tank 12, in which adsorption takes place as described in connection with FIG. 1. The adsorbent is routed into mixing tank 12 via conduit 13. The mixing of the suspension takes place with spiral-shaped mixing member 14 and the suspension is discharged from the mixing tank via discharge conduit 15.

FIG. 3 is a third alternative embodiment of the invention, in which both the reaction stage and the adsorption stage operate continuously. The feed of the extraction phase to be treated into mixing tank 16 can thus take place for example from a side stream of a metal extraction process. Hydroxylamine treatment takes place in mixing tank 16, of which there may be several connected in series in order to achieve a more favourable residence time distribution. The reaction stage mixing tank is also equipped with pH electrode 7 and mixer 17, which is preferably spiral in shape. The dispersion formed of the aqueous phase and the organic phase is routed via connecting channel 18 into settling section 19 of the reaction stage. To expedite the settling of the liquid phases, a fence made up of at least two plates is located in the settling section, between which the direction of flow of the extraction solution and the dispersion is changed temporarily, for instance to essentially vertical instead of the normal horizontal direction of flow. One such fence structure is disclosed in U.S. Pat. No. 7,465,402. In the drawing there are two fences, 20 and 21, but the number thereof may vary. Likewise the structure accordant with the invention is not restricted to this structure. The settling tank 19 has a collecting pipe 22 set in the lateral direction extending from one edge of the tank to the other near the bottom, with the purpose of recycling the hydroxylamine solution back to mixing tank 16 of the reaction stage. The settled and treated organic extraction solution is removed from the settling tank as overflow into extraction solution overflow launder 23. The remainder of the hydroxylamine-containing aqueous solution is recycled via aqueous solution collector apparatus 24 in the rear section of the settling tank back to mixing tank 16 or partially or completely to the hydroxylamine recovery treatment with cation exchange resin described above.

The settled extraction solution is routed from the reaction stage on to the adsorption stage via suitable launder structures, which are shown in the drawing in diagrammatic form only. These kinds of solutions are known in many present-day mixer-settler-extraction cells and they also enable the control of the surface height of the phases. The extraction solution is routed via connection pipe 25 to mixing tank 26 of the adsorption purification stage, in which the extraction solution adsorption stage takes place as a continuous operation. There may be several mixing tanks in series to achieve a more advantageous residence time distribution. An adsorbent is fed into the tank continuously via feed conduit 27 and the mixing of the suspension preferably occurs with a spiral-shaped mixing member 28. The suspension is routed via connection channel 29 to settling tank 30 of the adsorption stage, where the adsorbent settles to the bottom of the tank. The purified organic phase is removed via overflow launder 31 and discharge conduit 32 and may be routed back to the metal recovery process. The adsorbent is removed from the tank periodically or continuously by some suitable mechanism known in the art (not shown in detail in the drawing).

In all the alternatives pH measurement is carried out from the dispersion formed of the aqueous solution and organic phase by means of a pH electrode. It is the most advantageous method, but as stated above, obtaining a technically reliable measurement result from the dispersion may be difficult and pH measurement may also be taken from the aqueous solution of hydroxylamine compound to be fed into the mixing tank before it is fed into the tank or from the settled aqueous phase of the reaction stage.

If the stages according to the invention are implemented in the main stream of a metal recovery process, either the reaction stage settling tank or the adsorption purification stage settling tank or both together may function as the organic extraction solution storage tank.

The average residence time of the extraction phase in the reaction stage mixing tank in a continuous process is between 1 min and 2 h (preferably between 10 min-90 min) and in the adsorption stage mixing tank it is between 1 min-2 h (preferably between 2 min-60 min).

The method and equipment accordant with the invention may be used for restoring the working capacity of all extraction reagents containing a hydroxyoxime, and is not limited to the 5-nonyl salicylaldoxime-based extraction reagents used in the following examples. Thus the hydroxyoxime may also be a ketoxime. Likewise the molecule may be either a β-hydroxyoxime or an α-hydroxyoxime. Commercial hydroxyoximes are manufactured for instance under the brands Acorga® (Cytec Industries), LIX® (Cognis Corporation) and Chemorex® (Longlight International Limited).

The active extraction reagent in an extraction solution is dissolved in a suitable hydrocarbon solvent. There is a large number of this kind of non-water-soluble hydrocarbon solvent used in metal extraction. They include both aliphatic and aromatic hydrocarbons and mixtures thereof. The flash point of the solvents is typically above 70° C. Commercial solvents are available for instance under the following trademarks: Exxsol (Exxon Mobil Chemicals), NESSOL LIAV (Neste Oil), ORFOM (Chevron Phillips Chemical Company), Sasol Wax SSX (Sasol) and Shellsol (Shell Chemicals).

According to the invention, treating the extraction solution after the reaction stage in an adsorption stage is essential in order to remove the surface-active impurities that affect the settling of the phases. Even though bentonite was used in the following examples as the adsorbent, alternatively some other fine-ground clay mineral or diatomite could be used for the purpose. Clearly, in addition to these, other materials based on aluminium silicates, metal oxides, non-metal oxides, activated carbon, polymeric adsorbents or polymeric ion exchangers could also be relevant. Although a ground adsorbent was used in the examples, the shape or size of the material is not crucial, and the adsorbent may be a powder, or in spherical or fibre form.

EXAMPLES

Example 1

A test for regenerating an extraction reagent that had degraded chemically in process conditions was made in the laboratory. The original reagent concentration had been 36 volume % extraction reagent, of which the active component was 5-nonyl salicylaldoxime diluted in a commercial aliphatic hydrocarbon solvent. The organic solution also contained 2,2,4-trimethyl-1,2-pentanediol diisobutyrate, acting as the modifying agent. As a result of degradation, the 5-nonyl salicyialdoxime had reacted into the corresponding aldehyde i.e. 5-nonyl salicylaldehyde, which could be analysed quantitatively by means of gas chromatography analysis. Identification of the gas chromatogram peaks was done by means of a mass spectrometer. The change in the chemical composition of the extraction solution was also seen in the reduction of copper charging capacity from a value of 27 g/L to a value of 17 g/L and the growth in viscosity from a value of 10.5 mPas to a value of 13.7 mPas (25° C.).

First copper and other metals were stripped from the degraded extraction solution described above with sulphuric acid. 500 mL of this solution was routed into a thermostated 1000 mL glass reactor. 250 mL of aqueous solution was used for hydroxylamine treatment, into which 29.6 g of hydroxylamine sulphate had been leached, which theoretically was about twice the amount of the quantity of aldehyde contained in the extraction solution. The pH of the aqueous phase was raised to a value of 7.5 using $Na_2CO_3$ and the reaction was allowed to occur for 90 minutes at a temperature of 40° C. while mixing the dispersion with a 6-blade mixing member that had a diameter of 5.0 cm and a mixing speed of 520 rpm.

After the reaction, the aqueous phase was removed and approx. 1% by weight of Tonsil® Optimum 210 FF (Süd-Chemie AG) acid-activated calcium bentonite with a specific surface of about 200 $m^2/g$ was mixed into the organic phase. After an adsorption stage lasting approximately 30 minutes, the bentonite was separated from the solution by filtration.

The processed extraction phase was analysed by gas chromatograph and it was observed that the peaks of 5-nonyl salicylaldehyde were missing from the gas chromatogram and correspondingly, the peaks of 5-nonyl salicylaldoxime had grown. According to the analysis, treatment did not affect the concentration of 2,2,4-trimethyl-1,2-pentanediol diisobutyrate in the extraction solution in any way.

The copper charging capacity of the treated extraction solution was measured and it was observed that it had returned to a value of 27 g/L. After this, settling time tests were made at room temperature following the instructions in Acorga's "Standard Methods of Test". Tests were made in copper extraction conditions so that the copper concentration of the aqueous phase was 6.0 g/L and the pH 2.0. In all tests the organic phase was continuous. The reference test was made with an unused extraction reagent, which had a concentration of 27% by volume and where the active hydroxyoxime concentration and copper charging capacity were the same as those of the reagent that degraded in the process. The results are presented in Table 1.

TABLE 1

| Solution | Settling time(s) |
| --- | --- |
| Extraction solution degraded in process | 498 |
| Process solution, treated in the | |
| reaction stage only | 756 |
| adsorption stage only | 71 |
| both reaction and adsorption stages | 34 |
| Unused extraction solution | 37 |

Example 1 shows that, with the method accordant with the invention, the copper binding power of a hydroxyoxime reagent is restored to its original level. In addition, the settling tests indicate that a reaction stage alone is not sufficient, and an adsorption stage is essential for restoring the settling rate to the original one.

Example 2

An extraction solution degraded in the extraction process, in which the active component of the extractant was 5-nonyl salicylaldoxime, was treated batchwise in accordance with example 1, in a mixing tank having a volume of 10 $m^3$. The reaction conditions were as in example 1 other than that the temperature was 55° C. The adsorption stage was carried out in continuous operation in the adsorption section accordant with the principle of FIG. 3 so that the residence time of the extraction solution in the mixing tank was 45 min and the proportion of bentonite in the suspension was 1% by weight.

The dynamic viscosity of the extraction solution removed from the settling tank as overflow was measured and a value of 6.56 mPas (30.1° C.) was obtained, whereas before treatment it was 7.94 mPas.

The functionality of purified extraction solution in long-term use was studied in a pilot apparatus, which consisted of a DOP® pump (described in U.S. Pat. No. 5,662,871), two 275-litre spiral mixers connected in series and a 2.56 $m^3$ settler (depth of solution 1.6 m, width 0.4 m and length 4.0 m). The maximum flow of the apparatus was approx. 35 $m^3/h$, which allowed a settler load (i.e. flow rate in the settler in relation to the surface area of the settler) of 22 $m^3 m^{-2} h^{-1}$. Tests were made over 5 days with both untreated and treated extraction solution. The same copper sulphate solution was used continuously as the aqueous phase.

The separation of the phases was monitored by measuring the volume of the dispersion layer in the settler at different volume flow rates and phase continuities. Additionally, the A/O entrainment of the organic phase overflow was determined and correspondingly the O/A entrainment of the aqueous overflow. Table 2 presents as an example the results when the O/A ratio was 1 and when the continuous phase was aqueous. The results show that the treated extraction solution settled much more effectively than the original process solution used as reference. The possibility to load the extraction equipment more leads to greater production capacity. It also provides good grounds for the fact that extraction solution treatment with the method accordant with the invention is economically justified.

TABLE 2

| Settler load ($m^3 m^{-2} h^{-1}$) | Volume of dispersion ($m^3$) | A/O (ppm) | O/A (ppm) |
| --- | --- | --- | --- |
| Untreated solution | | | |
| 5.8 | 0.21 | 2500 | 3 |
| 7.09 | 0.41 | 5000 | 7.3 |
| 7.49 | 0.58 | 1100 | 2 |
| 8.63 | 0.54 | 3200 | 2 |
| 9.64 | 0.96 | 3900 | n.a |
| Treated solution | | | |
| 11.8 | 0.36 | 500 | n.a. |
| 12.9 | 0.42 | 150 | n.a. |
| 16.30 | 0.52 | 2300 | n.a. |
| 17.19 | 0.61 | 15000 | 5.1 |

Example 3

A test series for regenerating extraction solution by the method accordant with the invention was carried out in the same laboratory reactor as in example 1. The treated process solution was also the same as in example 1.

In the test series the significance of mixing on the progress of the hydroxylamine reaction was investigated first. The other conditions were as in example 1. The reactions were monitored by analysing the 5-nonyl salicylaldehyde concentration of samples taken of the reaction mixture at different times in two different tests at different mixing speeds by means of gas chromatography. The conversion of the reoximation reaction was calculated on the basis of the analyses. The results in FIG. 4 show that the reaction can be speeded up by effective mixing.

The significance of the hydroxylamine sulphate concentration is apparent from the test results in FIG. 5. The highest concentration of 2.25 mol/L is 370 g/L, in other words it is equivalent to a saturated solution. In other respects, the conditions correspond to those of example 1, except that the mixing speed was 600 rpm.

In addition, two tests were performed using hydroxylamine sulphate with a concentration of 2.25 mol/L. In one of the tests, the pH was raised with $Na_2CO_3$ to a value of 7.8 before the reaction was initiated, so that the reoximation proceeded to the end in about 20 minutes. In the other test no pH control was made at all, so the reaction was extremely slow and conversion was only 0.63 after 3 days. The results are shown in FIG. 6.

The test results of this example indicate that the test conditions have a conclusive effect on the reaction rate.

The examples show that the reaction times are significantly shorter than in earlier patent publications related to reoximation, which is a result of effective mixing combined with pH control.

Even though the treatment of the organic phase in the examples above with hydroxylamine solution and adsorption purification taking place in connection with it is described only using one commercial hydroxyoxime reagent mixture used in copper extraction, is it nevertheless clear that the method and equipment are applicable to all hydroxyoxime-based reagents. Likewise, the end-use of the reagents is not restricted to the extraction of copper; the application may be any metal or metalloid, such as for instance, nickel, palladium or germanium. In addition, the hydroxyoxime may be in a reagent mixture, in which the purpose of the hydroxyoxime is to affect the kinetics or equilibrium of the extraction.

Example 4

The reoximation stage was carried out in continuous flow mode in a laboratory mixer-settler type equipment consisting of a 500-mL first mixer, a 2300-mL second mixer which were followed by a 3400-mL settler. The treaded extractant phase was authentic degraded extractant from an industrial process. The extractant and the diluent were as in Example 1.

The organic flow rate was 170 mL/min while the aqueous phase was circulated at a flow rate of 100 mL/min. The aqueous phase inventory was 4.5 L and the initial hydroxylamine sulphate concentration was 1.28 mol/L.

Samples of the organic phase were taken from the settler launder and their aldehyde content were analyzed by gas chromatography. Correspondingly aqueous phase samples were taken from the circulation tank for the aqueous phase between the settler and the first-mixer and the hydroxylamine content of the samples were analyzed by acid-base titration.

The results based on samples collected during an experiment of 130 min long, are shown in FIG. 7. It demonstrates that the reoximation can be successfully carried out as a continuous operation. A stationary state is obtained after about 10 min when practically all the degraded extractant (i.e. the aldehyde form) has been reoximated. The reaction can be monitored also by the consumption of hydroxylamine (HAS) as shown in the Figure.

The invention claimed is:

1. A method of regenerating an organic extraction solution that has been used in a liquid-liquid extraction process, comprising:
    providing the organic extraction solution, wherein the organic extraction solution includes aldoximes and/or ketoximes, and wherein at least a portion of the aldoximes and/or ketoximes in the solution have been converted into aldehydes and/or ketones, respectively, during the liquid-liquid extraction process;
    reacting the organic extraction solution with an aqueous hydroxylamine solution to convert the aldehydes and/or ketones back into aldoximes and/or ketoximines, respectively, wherein the reacted organic extraction solution contains surface-active long-chain carboxylic acids that are formed during the reacting step;
    separating the reacted organic extraction solution and surface-active long-chain carboxylic acids from the aqueous hydroxylamine solution; and
    contacting the reacted organic extraction solution and surface-active long-chain carboxylic acids with an adsorption material to remove the surface-active long-chain carboxylic acids from the reacted organic extraction solution.

2. A method according to claim 1, wherein the adsorption material in solid form is at least one of the following: bentonite, diatomite, aluminium silicate, metal oxide, non-metal oxide, activated carbon, polymeric adsorbent and polymeric ion exchange resin.

3. A method according to claim 1, wherein the hydroxylamine is at least one of the following: hydroxylamine sulphate, hydroxylamine halide, hydroxylamine phosphate and hydroxylamine sulphonic acid.

4. A method according to claim 1, wherein a quantity of the hydroxylamine used in the reacting step is at least the equivalent of total quantity of the aldehyde and/or ketone formed in the reacted extraction solution.

5. A method according to claim 1, wherein a pH of the hydroxylamine-containing solution to be routed to the reacting step is regulated to the region of 1-10.

6. A method according to claim 1, wherein a pH of the hydroxylamine-containing solution to be routed to the reacting step is regulated to the region of 4-9.

7. A method according to claim 1, wherein at least one of the following is used for pH control of the hydroxylamine-containing solution: alkali-metal hydroxide, earth alkali metal hydroxide, alkali metal carbonate, earth alkali metal carbonate, ammonia and mineral acid.

8. A method according to claim 1, wherein the extraction solution is comprised of an extraction reagent and a hydrocarbon solvent, whereby the active metal-binding component of the extraction reagent is a hydroxy-oxime derivative, whose oxime group is either an aldoxime or ketoxime in structure.

9. A method according to claim 1, wherein the extraction solution is comprised of an extraction reagent and a hydrocarbon solvent, in addition to which there is an organic modifying agent in the extraction solution that includes at least one of the following: alcohol, phenol, ester, diester, ether, diether, ketone, amide and nitrile.

10. A method according to claim 1, wherein the hydroxylamine-containing aqueous solution is recycled in order to use the hydroxylamine or its compound effectively.

11. A method according to claim 1, wherein hydroxylamine is recovered from the hydroxylamine-containing aqueous solution by means of a cation exchange resin.

12. A method according to claim 1, wherein a concentration of hydroxylamine-containing aqueous solution is monitored by acid-base titration.

13. A method according to claim 1, wherein a quantity of the adsorption material used in the contacting step is 0.01-10 weight % of a combined weight of the reacted organic extraction solution, surface-active long-chain carboxylic acids, and adsorption material.

14. A method according to claim 1, wherein a quantity of the adsorption material used in the contacting step is 0.5-3 weight % of a combined weight of the reacted organic extraction solution, surface-active long-chain carboxylic acids, and adsorption material.

15. A method according to claim 1, wherein the adsorption material is separated from the extraction solution by settling, filtration or centrifugation.

16. A method according to claim 1, wherein the adsorption material is fed in ground form in the contacting step.

17. A method according to claim 1, wherein the adsorption material is fed as powder, spheres or filaments in the contacting step.

18. A method according to claim 1, wherein the reacting step and the contacting step take place as a batch operation.

19. A method according to claim 1, wherein the reacting step and the contacting step take place as a continuous operation.

20. A method according to claim 1, wherein the reacting step takes place as a batch operation, and the contacting step takes place as a continuous operation.

21. A method according to claim 1, wherein the reacting step takes place as a continuous operation and the contacting step takes place as a batch operation.

* * * * *